United States Patent [19]
Ryatt

[11] Patent Number: 5,701,886
[45] Date of Patent: Dec. 30, 1997

[54] TREATMENT NON-REBREATHER ASSEMBLY AND METHOD FOR DELIVERING OXYGEN AND MEDICATION

[76] Inventor: Sadie Ryatt, 5759 Willis Ave., Van Nuys, Calif. 91411

[21] Appl. No.: 511,745

[22] Filed: Aug. 7, 1995

[51] Int. Cl.$^6$ .................................................. A61M 15/00
[52] U.S. Cl. .................. 128/203.12; 128/200.14; 128/200.23; 128/203.28; 128/203.29
[58] Field of Search .................. 128/200.14, 200.23, 128/203.12, 203.28, 203.29, 204.11, 205.13, 205.17

[56] References Cited

U.S. PATENT DOCUMENTS

| | | | |
|---|---|---|---|
| 1,359,312 | 11/1920 | Bardwell | 128/203.29 |
| 1,998,327 | 4/1935 | McGuire | 128/203.29 |
| 2,535,938 | 12/1950 | Lombard | 128/205.25 |
| 3,490,452 | 1/1970 | Greenfield | 128/200.23 |
| 3,666,955 | 5/1972 | Suprenant et al. | 250/106 T |
| 4,433,684 | 2/1984 | Sarnoff et al. | 128/203.29 |
| 4,484,577 | 11/1984 | Sackner et al. | 128/203.29 |
| 4,598,704 | 7/1986 | Bordoni et al. | 128/200.14 |
| 4,809,692 | 3/1989 | Nowacki et al. | 128/203.29 |
| 4,829,998 | 5/1989 | Jackson | 128/203.15 |
| 4,841,953 | 6/1989 | Dodrill | 128/202.27 |
| 4,865,027 | 9/1989 | Laanen et al. | 128/203.29 |
| 4,886,055 | 12/1989 | Hoppough | 128/200.14 |
| 4,938,209 | 7/1990 | Fry | 128/203.29 |
| 5,018,519 | 5/1991 | Brown | 128/203.29 |
| 5,099,833 | 3/1992 | Michaels | 128/200.14 |
| 5,119,807 | 6/1992 | Roberts | 128/200.24 |
| 5,143,061 | 9/1992 | Kaimer | 128/205.25 |
| 5,357,945 | 10/1994 | Messina | 128/203.29 |
| 5,586,551 | 12/1996 | Hilliard | 128/203.29 |

*Primary Examiner*—Aaron J. Lewis
*Attorney, Agent, or Firm*—Flanagan & Flanagan; John K. Flanagan; John R. Flanagan

[57] ABSTRACT

A treatment non-rebreather assembly for the separate and simultaneous delivery of oxygen and an aerosolized medication to a patient basically includes a hollow connector tube with a transport body having an oxygen inlet port formed at one side portion of the body, a medication inlet port formed at another side portion of the body, a reservoir port formed at one end of the body for connecting to a reservoir bag and a patient outlet port formed at the opposite end of the body for connecting to a mask attachable about the head of a user. The assembly further includes a metered dose inhaler adapter for connecting the medication inlet port to an external source of aerosolized medication to permit the administration of the aerosolized medication to a patient through the connector tube. The assembly also has a releasable cap for closing the medication inlet port during non-use.

16 Claims, 2 Drawing Sheets

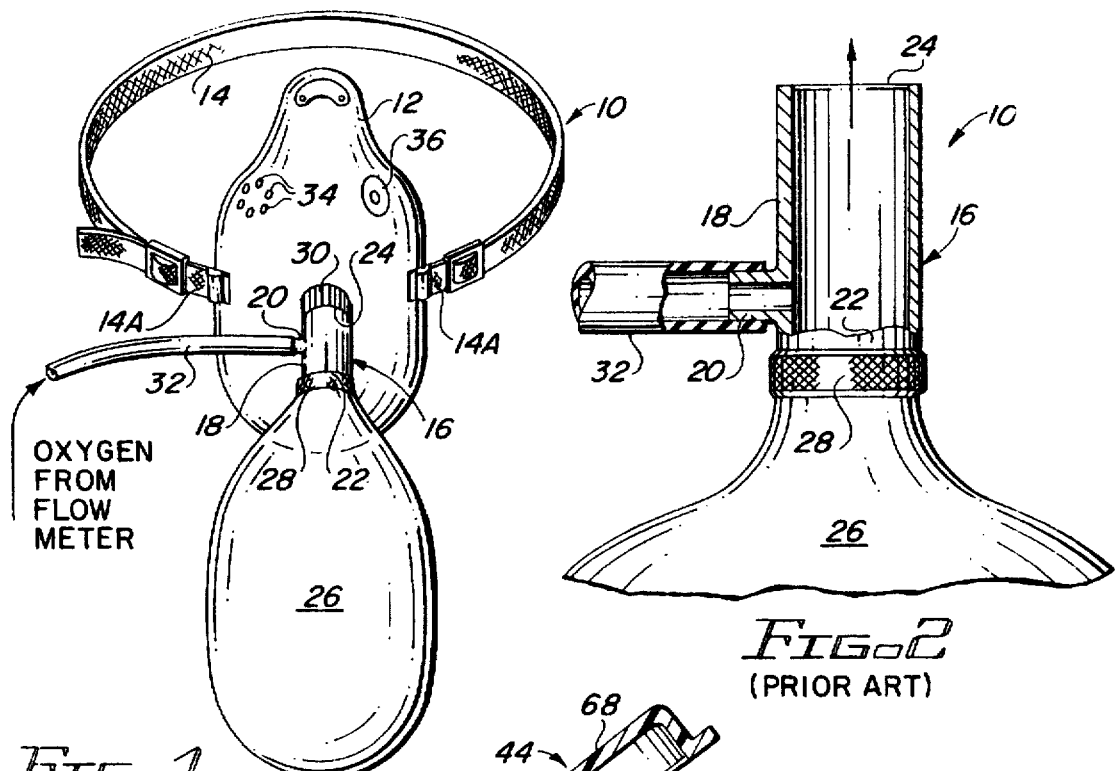
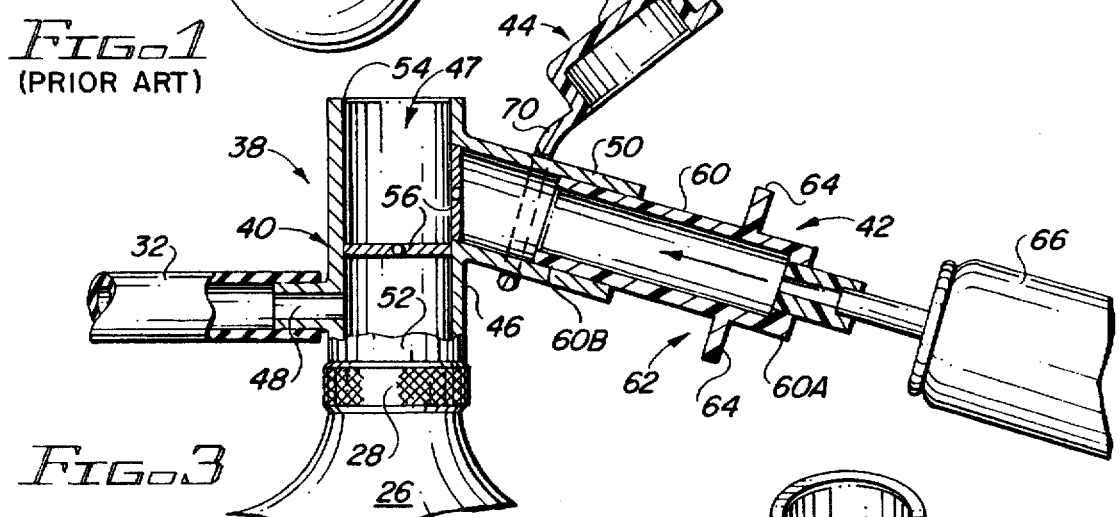
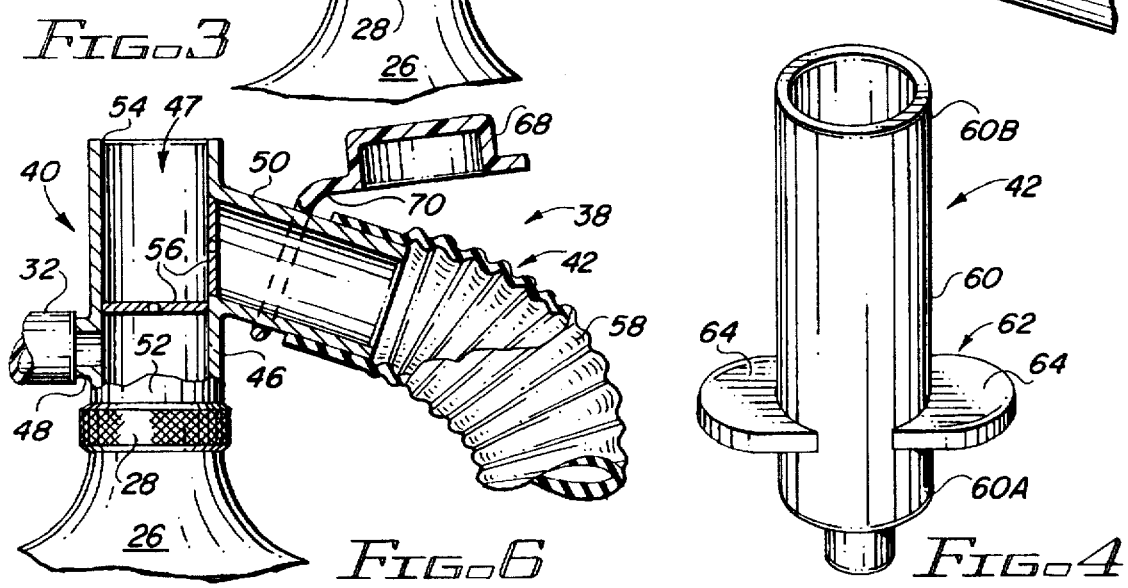

TREATMENT NON-REBREATHER ASSEMBLY AND METHOD FOR DELIVERING OXYGEN AND MEDICATION

BACKGROUND OF THE INVENTION

1. Field of the Invention

The present invention generally relates to gas inhalation devices and, more particularly, is concerned with a treatment non-rebreather assembly having separate inlet ports for the concurrent intake of oxygen and aerosolized medication and a method for delivering oxygen and medication to a patient using the treatment non-rebreather assembly.

2. Description of the Prior Art

For many years, a variety of respiratory inhaling devices have been used to deliver atomized treatments to patients. Many of these devices employ nebulizers which transform medications from their liquid to gaseous phase so as to enable a patient to intake by inhalation rather than by swallowing or injection. Respiratory and other types of ailments can be treated by this method. The aim of these devices is the efficient delivery to a patient of conditioned air while minimizing the relatively high levels of discomfort associated with using such devices.

Some patients require the delivery of both oxygen and an atomized medication at the same time. In these cases, it is often necessary to deliver each of the gases separately because a slight interruption in the delivery of oxygen may have harmful results. Each gas often must be given at a different dosage or rate from the other as well.

Most of the respiratory inhaling devices which have been developed thus far have at least one inlet port and employ a means such as a mask or mouthpiece to connect the device to a patient. Representative examples are disclosed in U.S. Pat. No. 3,666,955 to Suprenant et al., U.S. Pat. No. 4,433,684 to Sarnoff et al., U.S. Pat. No. 4,598,704 to Bordoni et al., U.S. Pat. No. 4,829,998 to Jackson, U.S. Pat. No. 4,865,027 to Laanen et al., U.S. Pat. No. 4,886,055 to Hoppough, U.S. Pat. No. 4,938,209 to Fry, U.S. Pat. No. 5,018,519 to Brown, U.S. Pat. No. 5,099,833 to Michaels and U.S. Pat. No. 5,119,807 to Roberts.

Of these examples, however, only the Laanen and Hoppough patents are directed to the administration of oxygen and an atomized therapeutic medication. The Laanen patent shows a therapeutic respiratory apparatus used to provide a continuous dosage of an aerosolized medicament to a patient. The apparatus has a nebulizer, a mask and a collapsible chamber. Oxygen may serve as a carrier gas supplied to the nebulizer which contains a reservoir of the liquid medicament. The aerosolized medicament is then delivered to a collapsible chamber which serves to store the aerosol between inhalations by a patient. The Hoppough patent shows an arrangement wherein humidified gas is supplied directly into a mask from a nebulizer device. The nebulizer device includes a fluid reservoir having a capillary tube. A duct sends oxygen past the upper opening of the tube so as to induce the drawing of fluid through the tube from the reservoir. The fluid is thus entrained in the oxygen supplied to a patient.

The problem with both of these devices, however, is that neither of them permit the separate and simultaneous transport of oxygen and an aerosolized medication by way of separate inlet ports. The dosage and rate of delivery of the oxygen and atomized medication therefore cannot be separately and simultaneously controlled.

Consequently, a need still exists for a relatively comfortable and efficient means for delivering oxygen and an aerosolized medication to a patient and in a way so as to permit each of the gases to be separately administered but at the same time.

SUMMARY OF THE INVENTION

The present invention provides a treatment non-rebreather assembly with dual gas inlet ports and an oxygen and medication delivering method and adapter designed to satisfy the aforementioned need. The principal advantage of the present invention is that it provides for the separate and simultaneous delivery of oxygen and an aerosolized medication to a patient.

Accordingly, the present invention is directed to a treatment non-rebreather assembly, which comprises: (a) a hollow connector tube including a transport body, an oxygen inlet port formed at one side portion of the body, an aerosolized medication inlet port formed at another side portion of the body, a reservoir port formed at one end of the body for connecting to a reservoir bag, and a patient outlet port formed at the opposite end of the body for connecting to means, such as a mask, for attaching the assembly to a patient's head; (b) means for connecting the medication inlet port to an external source of aerosolized medication to permit the delivery of the aerosolized medication to a patient through the connector tube; and (c) means for closing the medication inlet port during the non-use of the port.

Also, the connector tube includes one-way inhalation valves to control the direction of flow of the gases that enter through the inlet ports. The preferred means for connecting the connector tube to an external source of aerosolized medication is a hollow elongated sleeve with means for gripping the sleeve with fingers. The means for closing the medication inlet port is a releasable cap affixed to the outside of the medication inlet port. The cap fits over and encloses the opening of the medication inlet port when the port is not in use.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the following detailed description, reference will be made to the attached drawings in which:

FIG. 1 is a perspective view of a prior art connector tube having a single gas inlet port and being attached to a prior art inhalation mask.

FIG. 2 is an enlarged partially sectional view of the prior art connector tube of FIG. 1.

FIG. 3 is a sectional view of a preferred embodiment of the treatment non-rebreather assembly of the present invention used with a metered dose inhaler adapter of the present invention.

FIG. 4 is an enlarged perspective view of the metered dose inhaler adapter employed with the treatment non-rebreather assembly in FIG. 3.

FIG. 6 is a sectional view of the treatment non-rebreather assembly used with a conventional flexible hose instead of the metered dose inhaler adapter.

DETAILED DESCRIPTION OF THE INVENTION

Figure 5:
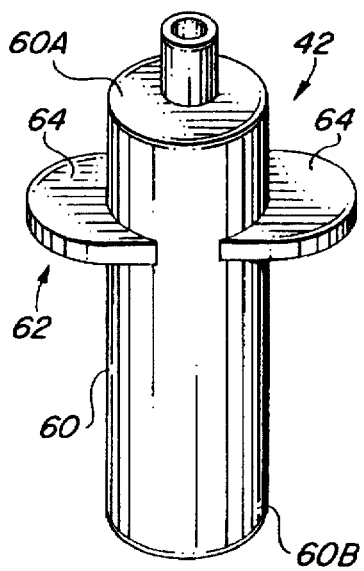
FIG. 5 is an inverted perspective view of the metered dose inhaler adapter shown in FIG. 4.

Referring to the drawings and particularly to FIGS. 1 and 2, there is illustrated a prior art inhalation device 10 which includes means in the form of a mask 12 and a strap 14 secured at opposite ends 14A to the opposite sides of the mask 12 for attaching the device 10 on the head of a patient, and a hollow connector tube 16 having a hollow transport body 18 and a single oxygen inlet port 20 connected to and extending outwardly from a side portion of the connector tube 16. The oxygen inlet port 20 is in the form of a hollow tubular nipple integrally attached to the side portion of the transport body 18 of the connector tube 16.

The connector tube 16 of the prior art inhalation device 10 also has a reservoir port 22 in the form of an opening defined at a lower end of the transport body 18 and a patient outlet port 24 in the form of an opening defined at the opposite upper end of transport body 18. The lower end of the transport body 18 is adapted for connection to a reservoir bag 26, while the upper end of the transport body 18 is adapted for connection to the mask 12, by any suitable means, such as complementary threads (not shown) formed on the exterior of the lower and upper ends of the transport body 18 and on the interiors of respective collars 28, 30 attached to the reservoir bag 26 and the mask 12. The oxygen inlet port 20 receives oxygen through a flexible tubing 32 having one end inserted in a frictional fitting relationship over the tubular nipple forming the oxygen inlet port 20. As is well known to one of ordinary skill in this art, the other end (not shown) of the flexible tubing 32 is typically coupled to an oxygen flow meter (not shown).

Thus, the oxygen flowing into the transport body 18 flows through the hollow body 18 to and through the lower reservoir port 22 to fill the reservoir bag 26 and to and through the upper patient outlet port 24 to the patient in response to inhalation by the patient. The mask 12 typically includes exhalation port holes 34 and a one-way exhalation valve 36 through which is exhausted carbon dioxide from the patient in response to exhalation by the patient. As described earlier, a major drawback with the above-described prior art inhalation device 10 is that the hollow connector tube 16 does not have another inlet port which can be used for the separate and simultaneous delivery of an aerosolized medication to the patient.

Figure 7:
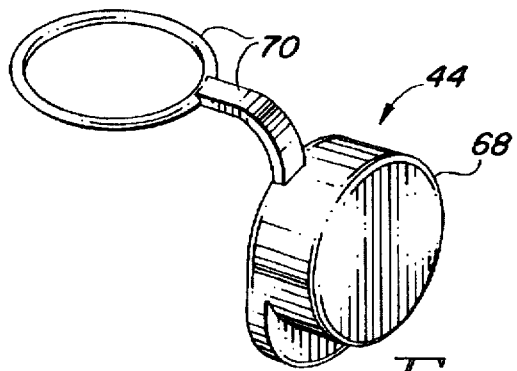
FIG. 7 is an enlarged perspective view of a releasable cap employed with the treatment non-rebreather assembly in FIGS. 3 and 6.

Referring now to FIGS. 3–7, there is illustrated a treatment non-rebreather assembly of the present invention, generally designated 38. The assembly 38, as will be described hereinafter, overcomes the problems associated with the prior art inhalation device 10 by being adaptable for use on a patient who must receive a continuous and uninterrupted flow of oxygen while simultaneously being administered an aerosolized medication. The treatment non-rebreather assembly 38 basically includes a hollow connector tube 40, a connecting means 42 and a removable closure 44.

Referring to FIGS. 3, 6, 8 and 9, the hollow connector tube 40 of the assembly 38 includes a transport body 46, defining a passageway 47 an oxygen inlet port 48 in the form of a hollow tubular nipple integrally connected to and extending outwardly from one side portion of the body 46, an aerosolized medication inlet port 50 in the form of another hollow tubular nipple integrally connected to and extending outwardly from another side portion of body 46, a reservoir port 52 in the form of an opening defined at a lower end of the body 46 for connecting to the prior art reservoir bag 26 in the same manner as the hollow connector tube 16 of the prior art inhalation device 10, and a patient outlet port 54 in the form of an opening defined at the upper opposite end of the body 46 for connecting to the prior art mask 12 in the same manner as the hollow connector tube 16 of the prior art inhalation device 10.

In the illustrated embodiment, the oxygen inlet port 48 of the connector tube 40 is situated closer to the reservoir bag 26 whereas medication inlet port 50 is situated closer to the patient outlet port 54 so as to keep the opposing gas flows from the respective ports 48, 50 from obstructing one another. The oxygen passing through the oxygen inlet port 48 tends to fill the reservoir bag 26 while the aerosolized medication passing through medication inlet port 50 tends to go directly to the patient as a result of the positioning of inlet ports 48, 50 on connector tube 40. Oxygen passing through oxygen inlet port 48 arrives by way of a system similar to that used in the prior art as shown in FIG. 1 wherein the flexible tubing 32 leads from an oxygen flow meter (not shown).

The treatment non-rebreather assembly 38 also includes one or more one-way inhalation valves 56 to control the direction of flow of gases that enter the connector tube 40 from the oxygen inlet port 48 and medication inlet port 50 and prevent the reverse flow of patient exhalation gases from patient outlet port 54 to oxygen inlet port 48 or medication inlet port 50. The valves 56 are illustrated in a simplified diagrammatic form, since they are of conventional construction per se and well-known to one of ordinary skill in this art.

FIGS. 3, 6 and 8 illustrate various selected placements of the valve or valves 56 with respect to the transport body 46 and the ports 48, 50. In FIGS. 3 and 6, the assembly 38 employs a pair of the one-way inhalation valves 56. In FIGS. 3 and 6, a pair of one-way inhalation valves 56 are employed. One of the valves 56 is located across the passageway 47 of the hollow transport body 46 just above the inner termination of the oxygen inlet port 48 and below the inner termination of the medication inlet port 50, whereas the other of the valves 56 is located across the inner termination of the medication inlet port 50. In FIG. 8, only a single one-way inhalation valve 56 is employed. The one valve 56 is located across the passageway 47 of the hollow transport body 46 just above the inner termination of the oxygen inlet port 48 and below the inner termination of the medication inlet port 50, while the other valve 56 is located across the inner termination of the medication inlet port 50.

Referring again to FIGS. 3 to 6, the connecting means 42 of the assembly 38 can take two different forms for connecting the medication inlet port 50 to an external source of aerosolized medication to permit the delivery of the aerosolized medication to a patient through the connector tube 40 of the assembly 38. In one embodiment shown in FIG. 6, connecting means 36 is a flexible tubing 58 which fits over the outer end and encloses the opening of the medication inlet port 50. In another embodiment shown in FIGS. 3 to 5, the connecting means 42 is a metered dose inhaler adapter which includes a hollow elongated sleeve 60 with a gripping means 62 for receiving a care giver's fingers to insert and withdraw the sleeve 60 relative to the medication inlet port 50. The sleeve 60 fits inside medication inlet port 50 to make a tight seal therewith. The sleeve 60 has a first open end 60A for the intake of an atomized medication and a second open end 60B for the release of the medication. The second open end 60B is wider than the first open end 60A. The gripping means 62 is in the form of a pair of tabs 64 attached to and projecting outwardly from opposite sides of the sleeve 60 adjacent to the first open end 60A thereof. The pair of tabs 64 are located closer to first open end 60A than to second open end 60B of the sleeve 60. The index and middle finger of a care giver grip the tabs 64 while the thumb pushes on a metered dose inhaler 66, as shown in FIG. 3, so as to discharge medication from a chamber of metered dose inhaler 66 into the medication inlet port 50. The first open end 60A of sleeve 60 is shaped so as to enable the sleeve 60 to receive the discharging end of metered dose inhaler 66 and thereby to permit the delivery of medication into connector tube 40 by way of medication inlet port 50.

Figure 8:
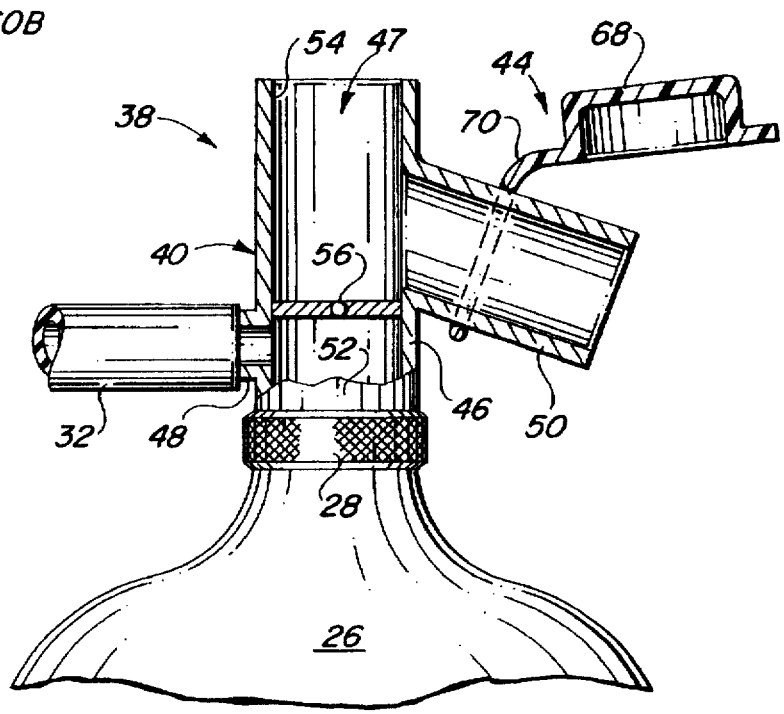
FIG. 8 is a sectional view of the treatment non-rebreather assembly similar to that of FIGS. 3 and 6 but showing only a single one-way inhalation valve used in the assembly.

Referring to FIGS. 3 and 6–8, the closure 44 of the assembly 38 is used for sealably closing the medication inlet port 50 during periods of non-use thereof. The closure 44 preferably takes the form of a releasable cap 68 flexibly attached to a circular ring or band 70 which is slidably fitted over the outside of the medication inlet port 50. The releasable cap 68 fits over and encloses the outer open end of the medication inlet port 50. The band 70 holds the cap 68 when the port 50 is in use so that the cap 68 cannot become displaced from the connector tube 40.

It is thought that the present invention and its advantages will be understood from the foregoing description and it will be apparent that various changes may be made thereto without departing from the spirit and scope of the invention or sacrificing all of its material advantages, the form hereinbefore described being merely preferred or exemplary embodiment thereof.

I claim:

1. A treatment non-rebreather assembly for the separate and simultaneous administration of oxygen and an aerosolized medication to a patient, comprising:
   (a) a hollow connector tube including
      (i) a transport body having one end and an opposite end and one side portion and another side portion, said transport body defining a passageway extending between said one and opposite ends,
      (ii) an oxygen inlet port formed at said one side portion of said body,
      (iii) an aerosolized medication inlet port formed at said another side portion of said body,
      (iv) a reservoir port formed at said one end of said body for connecting to a reservoir bag,
      (v) a patient outlet port formed at said opposite end of said body for connecting to means for attaching said assembly to a patient, and
      (vi) a single one-way inhalation valve located across said passageway of said transport body between said oxygen inlet port and said medication inlet port and adapted to limit direction of flow to being from said reservoir port toward said patient outlet port;
   (b) means for connecting said medication inlet port to an external source of an aerosolized medication to permit the delivery of the aerosolized medication to a patient through said connector tube; and
   (c) means for closing said medication inlet port during the non-use of said port.

2. The assembly of claim 1 wherein said oxygen inlet port is positioned closer to said reservoir port on said connector tube than to said patient outlet port thereon and said medication inlet port is positioned closer to said patient outlet port on said connector tube than to said reservoir port thereon so as to prevent opposing flows from said oxygen inlet port and said medication inlet port from obstructing one another.

3. The assembly of claim 1 wherein said oxygen inlet port is positioned closer to said reservoir port on said connector tube than to said patient outlet port thereon such that oxygen arriving from said oxygen inlet port tends to flow to said reservoir port.

4. The assembly of claim 1 wherein said medication inlet port is positioned closer to said patient outlet port on said connector tube than to said reservoir port thereon such that said aerosolized medication arriving from said medication inlet port tends to go directly to the patient.

5. The assembly of claim 1 wherein said means for connecting said medication inlet port to the external source of aerosolized medication is a flexible tubing.

6. The assembly of claim 1 wherein said means for connecting said medication inlet port to the external source of aerosolized medication is a hollow elongated sleeve having means for gripping with fingers and being connectable to said medication inlet port to permit the delivery of an aerosolized medication to a patient through said connector tube.

7. The assembly of claim 6 wherein said means for gripping said sleeve is a pair of tabs attached to and projecting from opposite sides of said sleeve.

8. The assembly of claim 7 wherein said pair of tabs is located closer to one end than to a opposite end of said sleeve.

9. The assembly of claim 1 wherein said means for closing said medication inlet port during non-use of said port is a releasable cap attached to said port to fit over said port opening.

10. The assembly of claim 9 wherein said cap is secured to the outside of said medication inlet port by a ring that is fitted around said port which holds said cap when said port is in use.

11. A treatment non-rebreather assembly for the separate and simultaneous administration of oxygen and an aerosolized medication to a patient, comprising:
   (a) a hollow connector tube including
      (i) a transport body having one end and an opposite end and one side portion and another side portion, said transport body defining a passageway extending between said one and opposite ends,
      (ii) an oxygen inlet port formed at said one side portion of said body,
      (iii) an aerosolized medication inlet port formed at said another side portion of said body,
      (iv) a reservoir port formed at said one end of said body for connecting to a reservoir bag,
      (v) a patient outlet port formed at said opposite end of said body for connecting to means for attaching said assembly to a patient, and
      (vi) a pair of one-way inhalation valves, a first of said valves being located across said passageway of said transport body between said oxygen inlet port and said medication inlet port and adapted to limit direction of flow to being from said reservoir port toward said patient outlet port, a second of said valves being located at said medication inlet port and adapted to limit direction of flow to being into said transport body through said medication inlet port;
   (b) means for connecting said medication inlet port to an external source of an aerosolized medication to permit the delivery of the aerosolized medication to a patient through said connector tube; and
   (c) means for closing said medication inlet port during the non-use of said port.

12. The assembly of claim 11 wherein said oxygen inlet port is positioned closer to said reservoir port on said connector tube than to said patient outlet port thereon and said medication inlet port is positioned closer to said patient outlet port on said connector tube than to said reservoir port thereon so as to prevent opposing flows from said oxygen inlet port and said medication inlet port from obstructing one another.

13. A treatment non-rebreather assembly for the separate and simultaneous administration of oxygen and an aerosolized medication to a patient, comprising:

(a) a hollow connector tube including
 (i) a transport body having one end and an opposite end and one side portion and another side portion, said transport body defining a passageway extending between said one and opposite ends,
 (ii) an oxygen inlet port formed at said one side portion of said transport body and opening into said passageway,
 (iii) an aerosolized medication inlet port formed at said another side portion of said transport body and opening into said passageway,
 (iv) a reservoir port forming an opening at said one end of said transport body for connecting said passageway thereof in communication with an external reservoir bag, and
 (v) a patient outlet port forming an opening at said opposite end of said transport body for connecting said passageway thereof to means for attaching said assembly to a patient;

(b) means for connecting said medication inlet port to an external source of an aerosolized medication to permit the delivery of the aerosolized medication to a patient through said connector tube; and (c) means for closing said medication inlet port during the non-use of said port.

14. The assembly of claim 13 wherein said oxygen inlet port is positioned closer to said reservoir port on said connector tube than to said patient outlet port thereon and said medication inlet port is positioned closer to said patient outlet port on said connector tube than to said reservoir port thereon so as to prevent opposing flows from said oxygen inlet port and said medication inlet port from obstructing one another.

15. The assembly of claim 13 wherein said oxygen inlet port is positioned closer to said reservoir port on said connector tube than to said patient outlet port thereon such that oxygen arriving from said oxygen inlet port tends to flow to said reservoir port.

16. The assembly of claim 13 wherein said medication inlet port is positioned closer to said patient outlet port on said connector tube than to said reservoir port thereon such that said aerosolized medication arriving from said medication inlet port tends to go directly to the patient.

* * * * *